(12) United States Patent
Xie

(10) Patent No.: US 11,446,659 B2
(45) Date of Patent: Sep. 20, 2022

(54) NUCLEIC ACID EXTRACTION APPARATUS

(71) Applicant: HANGZHOU BIGFISH BIO-TECH CO., LTD., Hangzhou (CN)

(72) Inventor: Lianyi Xie, Hangzhou (CN)

(73) Assignee: HANGZHOU BIGFISH BIO-TECH CO., LTD., Hangzhou (CN)

( * ) Notice: Subject to any disclaimer, the term of this patent is extended or adjusted under 35 U.S.C. 154(b) by 103 days.

(21) Appl. No.: 16/525,197

(22) Filed: Jul. 29, 2019

(65) Prior Publication Data
US 2020/0164370 A1    May 28, 2020

(30) Foreign Application Priority Data

Nov. 26, 2018   (CN) .......................... 201811470025.2

(51) Int. Cl.
| | |
|---|---|
| *B01L 3/00* | (2006.01) |
| *C12Q 1/6844* | (2018.01) |
| *C12Q 1/6848* | (2018.01) |
| *C12Q 1/6806* | (2018.01) |

(52) U.S. Cl.
CPC ...... *B01L 3/502715* (2013.01); *C12Q 1/6806* (2013.01); *C12Q 1/6846* (2013.01); *C12Q 1/6848* (2013.01); *B01L 2400/0478* (2013.01)

(58) Field of Classification Search
USPC ..................................................... 435/287.2
See application file for complete search history.

(56) References Cited

U.S. PATENT DOCUMENTS

| | | | | |
|---|---|---|---|---|
| 2003/0162304 | A1* | 8/2003 | Dority | B01L 3/50273 436/164 |
| 2013/0280725 | A1* | 10/2013 | Ismagilov | B01L 3/50273 435/6.12 |
| 2015/0209789 | A1* | 7/2015 | Kho | B01L 3/523 435/287.2 |
| 2015/0275292 | A1* | 10/2015 | Chiang | B01L 3/502 506/9 |
| 2016/0186240 | A1* | 6/2016 | Andreyev | B01L 7/525 435/287.2 |
| 2017/0016052 | A1* | 1/2017 | Cooney | G01N 33/54386 |
| 2017/0292151 | A1* | 10/2017 | Connolly | C12Q 1/6825 |
| 2018/0187243 | A1* | 7/2018 | Smith | C12Q 1/6851 |

FOREIGN PATENT DOCUMENTS

| | | | |
|---|---|---|---|
| KR | 20180125814 | * | 11/2018 |
| KR | 1020180125814 | * | 11/2018 |

* cited by examiner

*Primary Examiner* — Holly Kipouros
*Assistant Examiner* — Nathan G Esperon
(74) *Attorney, Agent, or Firm* — NZ Carr Law Office

(57) ABSTRACT

The present invention discloses a nucleic acid extraction apparatus and a method using the apparatus for extracting nucleic acids and amplifying target nucleic acids. The nucleic acid extraction apparatus comprising: a nucleic acid extraction element, a waste storage chamber, and a reaction chamber, wherein the reaction chamber is selectively in communication with the nucleic acid extraction element and the waste storage chamber, and the apparatus realizes fluid exchange through the pressure between the waste storage chamber and the reaction chamber. In the present invention, by using an integrated control system, the conventional manual process of nucleic acid extraction and purification is integrated into a fully automatic closed process, making the operation more conveniently and quickly and improving the efficiency of experimental work.

8 Claims, 8 Drawing Sheets

NUCLEIC ACID EXTRACTION APPARATUS

CROSS REFERENCE TO RELATED APPLICATION

The present application claims the benefit of Chinese Patent Application No. 201811470025.2, filed on Nov. 26, 2018. The content of this application including all tables, diagrams and claims is incorporated hereby as reference in its entity.

FIELD OF THE INVENTION

The present invention relates to a field of biological detection, and in particular to a nucleic acid extraction apparatus and a method using the apparatus for extracting nucleic acids and amplifying target nucleic acids.

BACKGROUND OF THE INVENTION

Nucleic acids are the basis for studies in molecular biology field. High-quality nucleic acids are essential for the studies of molecular markers, gene cloning and gene expressions, etc. As biological samples (such as blood, saliva, semen, or other secretions) are complex in composition, generally it is required to carry out extraction, purification and amplification of target nucleic acids before subsequent studies. At present, the existing nucleic acid extraction and amplification mainly have the following problems: first, due to large number of samples, complicated sample processing, nucleic acid extraction, purification and amplification steps, the manual operations may produce errors and make the operations to be more complicated, thus it is unable to perform efficient and rapid extraction and amplification of target nucleic acids; second, most of molecular diagnostics need to be carried out in the laboratory, and many grassroots units cannot establish a standard molecular diagnostic laboratory, moreover, operators have different operating habits and proficiency, which may cause cross-contamination of samples during extraction and amplification of nucleic acids; third, existing instruments and apparatus for nucleic acid extraction and PCR are often large in size and not suitable for use at sampling sites, which limits the applications of molecular diagnostics to some extent. The automatic, closed and integrated operation of nucleic acid extraction and amplification can shorten the related process and reduce human influence and enhance the safety and effectiveness of preparation of nucleic acid samples, and in addition, it can meet the requirements for small and portable apparatus for the rapid detections in the grassroots units or on the sites.

U.S. Pat. No. 9,212,980 discloses an apparatus for nucleic acid extraction and amplification comprising a plurality of chambers, a fluid displacement region and a fluid processing region, wherein the fluid processing region is provided with a fluid processing material for cell capture, cell lysis, binding analytes, etc., such as a filter. The fluid displacement region is used to temporarily store fluids and it is in communication with the fluid processing region. During use, by adjusting the position of a rotary valve, the fluid processing region is selectively in communication with the plurality of chambers, thus the fluid is driven to flow between the fluid processing region, the fluid displacement region and chambers by up and down movement of a piston. In this process, the fluid is controlled by a pair of ports of the valve body. By rotating the valve body, the two ports selectively communicate with the chambers in sequence to cause fluid displacement or movement, which may result in cross-contamination of samples in several channels, affecting the efficiency of DNA amplification. In addition, when performing DNA extraction, for example, biological cells are immobilized in the fluid processing region by a fluid processing material such as a filter, and by pushing the piston down, the washing liquid and lysate sequentially flow through the fluid processing region to lyse the biological cells and release the intracellular DNA. Due to the presence of negative pressure in the fluid displacement region and the waste chamber and the clogging of the filter by the broken biological cells and tissues, etc., the fluid is difficult to be discharged from the fluid displacement region when the piston and it is required to apply a great push force, which is not easy to operate. Moreover, after the biological cells are lysed, the intracellular DNA is mixed with the tiny biological tissues that cannot be adsorbed or filtered by the filter, and the lysate directly enters the reagent chamber to mix with the amplification reagents, resulting in insufficient purity of the extracted template DNA and adverse effect on PCR results.

SUMMARY OF THE INVENTION

In view of the shortcomings of the prior art, it is an object of the present invention to provide a nucleic acid extraction apparatus. The present invention can realize convenient and miniaturized extraction of DNA and achieve the purpose of functional integration, structural miniaturization and automatic extraction of DNA through a microfluidic DNA extraction module.

In a first aspect, the present invention provides a nucleic acid extraction apparatus, comprising:

a nucleic acid extraction element, a waste storage chamber, and a reaction chamber, wherein the reaction chamber is selectively in communication with the nucleic acid extraction element and the waste storage chamber, and the apparatus realizes fluid exchange through the pressure between the waste storage chamber and the reaction chamber.

As used herein, "fluid exchange" means that fluid can flow from one place to another. In the present invention, it means that fluid can enter a reaction chamber from a nucleic acid extraction element or a waste storage chamber, or can enter a nucleic acid extraction element or a waste storage chamber from a reaction chamber, to achieve repeatedly switch between these chambers.

As used herein, "selectively" means that the waste storage chamber is not in fluidic communication with the reaction chamber when the reaction chamber is in fluidic communication with the nucleic acid extraction element; and the reaction chamber is not in fluidic communication with the nucleic acid extraction element when the waste storage chamber is in fluidic communication with the reaction chamber, that is, the reaction chamber is selectively in fluidic communication with the nucleic acid extraction element or in fluidic communication with the waste storage chamber when appropriate.

Preferably, for the apparatus, fluid enters the waste storage chamber from the reaction chamber by reducing the air pressure of the waste storage chamber.

Preferably, the air pressure of the waste storage chamber for the apparatus is reduced by a venting element that is in communication with the waste storage chamber.

Preferably, the venting element is a columnar suction column.

Preferably, the venting element is a cylindrical suction column.

Preferably, a gasket is disposed at the junction of the suction column and the waste liquid storage chamber.

Preferably, a solid phase material for nucleic acid extraction is disposed in the reaction chamber.

Preferably, the solid phase material for nucleic acid extraction is a magnetic bead.

When the solid phase material for nucleic acid extraction is a magnetic bead, the reaction chamber has a permanent magnet, and the magnetic bead is fixed in the reaction chamber. The magnetic bead can specifically bind to free DNAs to form a magnetic bead-DNA complex; accordingly, DNAs are immobilized in the reaction chamber.

Preferably, the nucleic acid extraction element comprises:
a lysis chamber for adding and storing a mixture of sample and lysate; or,
a wash chamber for adding and storing washing liquid; or,
an eluent chamber for adding and storing eluent;
wherein, one or more of the lysis chamber, the wash chamber or the eluent chamber are in fluidic communication with the reaction chamber, respectively.

Preferably, the wash chamber comprises a primary wash chamber, a secondary wash chamber and a tertiary wash chamber, one or more of the primary wash chamber, the secondary wash chamber or the tertiary wash chamber being in fluidic communication with the reaction chamber, respectively.

It is to be understood that the apparatus described herein may comprise a plurality of wash chambers, for example, two, three, four, five, etc., to satisfy nucleic acid purification using a plurality of different washing liquids, or to use a larger amount of the same washing liquid to perform washing, to improve the purity of nucleic acids.

Preferably, the apparatus may further comprise a nucleic acid amplification element, and the nucleic acid amplification element is a PCR reaction solution chamber that is in fluidic communication with the reaction chamber, inside of which is provided with reagents for a PCR reaction.

Preferably, the nucleic acid amplification element further comprises a PCR reaction tube that is in fluidic communication with the PCR reaction solution chamber.

Preferably, the sidewall of the PCR reaction solution chamber is provided with an input port and a discharge port that are in fluidic communication with the PCR reaction tube.

Preferably, the PCR reaction solution chamber comprises a primary PCR reaction solution chamber and a secondary PCR reaction solution chamber, wherein the primary PCR reaction solution chamber is in fluidic communication with the reaction chamber, wherein an input port is disposed at the bottom of the sidewall of the primary PCR reaction solution chamber, and a discharge port disposed at the top of the sidewall of the secondary PCR reaction solution chamber. The mixture of the PCR reaction solution and the nucleic acids enters the PCR reaction tube from the input port at the bottom of the sidewall of the primary PCR reaction solution chamber. As the liquid enters, the air in the PCR reaction tube is discharged from the discharge port at the top of the sidewall of the secondary PCR reaction solution chamber, so as to allow the mixture to enter smoothly.

Preferably, the apparatus comprises a microfluidic channel for fluidic communication with a reaction chamber, a waste storage chamber, a nucleic acid extraction element or a nucleic acid amplification element.

Preferably, the microfluidic channel is radially extended on a rotary disk, and the reaction chamber, the waste storage chamber, the nucleic acid extraction element or the nucleic acid amplification element are in communication with or not in communication with each other by the rotation of the rotary disk.

Preferably, the fluid exchange is achieved by a microfluidic channel.

Preferably, wherein the waste storage chamber is not in fluidic communication with the reaction chamber when the reaction chamber is in fluidic communication with the nucleic acid extraction element; and the reaction chamber is not in fluidic communication with the nucleic acid extraction element when the waste storage chamber is in fluidic communication with the reaction chamber.

Preferably, wherein the apparatus comprises a piston, the fluid in the nucleic acid extraction element enters the reaction chamber by the movement of the piston.

Preferably, wherein the movement of the piston is an upward movement along the reaction chamber.

Preferably, the apparatus further comprises a venting element that causes the waste storage chamber to generate a negative pressure, thereby allowing the fluid in the reaction chamber to enter the waste storage chamber.

Preferably, wherein the negative pressure drives the piston to move downwardly along the reaction chamber.

Preferably, wherein the venting element that causes the waste storage chamber to generate a negative pressure is a suction column connected to the waste storage chamber.

In a second aspect, the present invention provides a method for extracting a nucleic acid and amplifying a specific target nucleic acid using a portable apparatus.

Preferably, the method comprises the following steps:
(1) providing a nucleic acid extraction apparatus, wherein the apparatus comprising:
a nucleic acid extraction element for extraction of nucleic acids;
a waste storage chamber for storing waste liquid during the reaction;
a reaction chamber, being selectivity in communication with the nucleic acid extraction element and the waste storage chamber;
(2) allowing the reaction chamber to be in fluidic exchange with the waste storage chamber or the nucleic acid extraction element to achieve extraction of nucleic acids.

Preferably, the fluid is exchanged between the reaction chamber, the waste storage chamber, or the nucleic acid extraction element by a pressure change between the waste storage chamber and the reaction chamber.

Preferably, the fluid is allowed to enter the waste storage chamber from the reaction chamber by reducing the air pressure in the waste storage chamber.

Preferably, the air pressure of the waste storage chamber is reduced by a venting element that is in communication with the waste storage chamber.

Preferably, the venting element is a cylindrical suction column.

Preferably, a solid phase material for nucleic acid extraction is provided in the reaction chamber to bind the nucleic acid in the sample to the solid phase material for nucleic acid extraction.

Preferably, the solid phase material for nucleic acid extraction is a magnetic bead.

Preferably, the nucleic acid extraction element comprises:
a lysis chamber for adding and storing a mixture of sample and lysate; or,
a wash chamber for adding and storing washing liquid; or,
an eluent chamber for adding and storing eluent;

wherein, one or more of the lysis chamber, the wash chamber or the eluent chamber are in fluidic communication with the reaction chamber, respectively.

Preferably, the wash chamber comprises a primary wash chamber, a secondary wash chamber and a tertiary wash chamber, one or more of the primary wash chamber, the secondary wash chamber or the tertiary wash chamber being in fluidic communication with the reaction chamber, respectively.

Preferably, the method further comprises a step of nucleic acid amplification, and the reaction chamber is in fluidic communication with the nucleic acid amplification element to achieve nucleic acid amplification, wherein, the nucleic acid amplification element is a PCR reaction solution chamber that is in fluidic communication with the reaction chamber, inside of which is provided with reagents for a PCR reaction.

Preferably, the nucleic acid amplification element further comprises a PCR reaction tube that is in fluidic communication with the PCR reaction solution chamber, to allow fluid to enter the PCR reaction tube for amplification reaction.

Preferably, the PCR reaction tube achieves fluidic communication through an input port and a discharge port disposed on sidewall of the PCR reaction solution chamber.

Preferably, the PCR reaction solution chamber comprises a primary PCR reaction solution chamber and a secondary PCR reaction solution chamber, wherein the primary PCR reaction solution chamber is in fluidic communication with the reaction chamber, wherein an input port is disposed at the bottom of the sidewall of the primary PCR reaction solution chamber, and a discharge port disposed at the top of the sidewall of the secondary PCR reaction solution chamber.

Preferably, fluidic communication or exchange between the reaction chamber, the waste storage chamber, the nucleic acid extraction element or the nucleic acid amplification element is achieved by a microfluidic channel disposed on the nucleic acid extraction apparatus.

Preferably, the microfluidic channel is radially extended on a rotary disk, and the reaction chamber, the waste storage chamber, the nucleic acid extraction element or the nucleic acid amplification element are in communication with or not in communication with each other by the rotation of the rotary disk.

Preferably, the fluid exchange is achieved by a microfluidic channel.

Preferably, wherein the waste storage chamber is not in fluidic communication with the reaction chamber when the reaction chamber is in fluidic communication with the nucleic acid extraction element; and the reaction chamber is not in fluidic communication with the nucleic acid extraction element when the waste storage chamber is in fluidic communication with the reaction chamber.

Preferably, wherein the fluid in the nucleic acid extraction element enters the reaction chamber by the movement of a piston disposed on the reaction chamber.

Preferably, wherein the movement of the piston is an upward movement along the reaction chamber.

Preferably, wherein the fluid in the reaction chamber enters the waste storage chamber by a venting element that causes the waste storage chamber to generate a negative pressure.

Preferably, wherein the venting element that causes the waste storage chamber to generate a negative pressure is a suction column connected to the waste storage chamber, and the negative pressure drives the piston to move downwardly along the reaction chamber.

In a third aspect, the present invention provides a nucleic acid extraction apparatus. Preferably, the apparatus comprises a nucleic acid extraction element, a waste storage chamber, and a reaction chamber, wherein the reaction chamber is selectively in fluidic communication with the nucleic acid extraction element or the waste storage chamber through a microfluidic channel.

Preferably, the microfluidic channel comprises an inlet microfluidic channel that allows the reaction chamber to be in fluidic communication with the nucleic acid extraction element, and a plurality of outlet microfluidic channels that allow the reaction chamber to be in fluidic communication with the waste storage chamber.

Preferably, wherein the waste storage chamber is not in fluidic communication with the reaction chamber when the reaction chamber is in fluidic communication with the nucleic acid extraction element via the inlet microfluidic channel; and the reaction chamber is not in fluidic communication with the nucleic acid extraction element when the waste storage chamber is in fluidic communication with the reaction chamber via the outlet microfluidic channel.

Preferably, the microfluidic channel is radially extended on a rotary disk, and the reaction chamber, the waste storage chamber, the nucleic acid extraction element are in communication with or not in communication with each other by the rotation of the rotary disk.

Preferably, the inlet microfluidic channel is different in length from the outlet microfluidic channel.

Preferably, the nucleic acid extraction element comprises: a lysis chamber, a wash chamber or an eluent chamber, wherein one or more of the lysis chamber, the wash chamber or the eluent chamber being in fluidic communication with the reaction chamber via the inlet microfluidic channel respectively.

Preferably, the wash chamber comprises a primary wash chamber, a secondary wash chamber and a tertiary wash chamber, wherein, one or more of the primary wash chamber, the secondary wash chamber or the tertiary wash chamber being in fluidic communication with the reaction chamber via the inlet microfluidic channel respectively.

Preferably, the apparatus may further comprise a nucleic acid amplification element, and the nucleic acid amplification element is a PCR reaction solution chamber that is in communication with the reaction chamber, inside of which is provided with reagents for a PCR reaction.

Preferably, the PCR reaction solution chamber is in fluidic communication with the reaction chamber via an inlet microfluidic channel.

In a fourth aspect, the present invention provides a nucleic acid extraction apparatus. Preferably, the apparatus comprises: a nucleic acid extraction element, a waste storage chamber, a nucleic acid amplification element, and a reaction chamber, wherein the nucleic acid amplification element comprises a PCR reaction solution chamber and a PCR reaction tube, and an input port and a discharge port are provided on the sidewall of the PCR reaction solution chamber for communicating with the PCR reaction tube.

Preferably, the PCR reaction solution chamber comprises a primary PCR reaction solution chamber and a secondary PCR reaction solution chamber, the input port is disposed at the bottom of the sidewall of the primary PCR reaction solution chamber, and the discharge port is disposed at the top of the sidewall of the secondary PCR reaction solution chamber.

Preferably, the input port is a through hole, which is in communication with a first port of a PCR reaction tube injection channel, for injecting a fluid into a PCR reaction tube; the discharge port is a through hole, which is in communication with a second port of a PCR reaction tube injection channel, for discharging the gas in the channel.

Preferably, the apertures of the input port and the discharge port are smaller than the apertures of the first port and the second port.

Preferably, the apparatus is provided with a seal at the junction of the PCR reaction solution chamber and the PCR reaction tube.

Preferably, the seal has two through holes, wherein the size of the through hole connected between the seal and the PCR reaction solution chamber corresponds to the size of the input port and the discharge port, and the size of the through hole connected between the seal and the PCR reaction tube corresponds to the size of the first port and the second port.

Preferably, the seal is made of an elastic material.

Preferably, the seal is made of silica gel.

Preferably, a non-absorbent material capable of slowly leaking gas is provided at the top of the primary PCR reaction solution chamber.

Preferably, the non-absorbent material capable of slowly leaking gas is high-density hydrophobic cotton.

The present invention can achieve the following beneficial effects:

(1) The present invention adopts a reaction chamber having a hollow piston and a hollow receiving chamber for extraction and purification of nucleic acids in samples. The magnetic bead is fixed to a reaction chamber by a permanent magnet disposed in a hollow receiving chamber, so that the nucleic acids released after lysis of samples are specifically immobilized in the reaction chamber, and with the up and down movement of the hollow piston, the integrated operation of nucleic acid extraction and purification can be realized. In the present invention, a magnetic bead is used as a solid phase material for nucleic acid extraction. When the permanent magnet is removed, the magnetic bead which binds the nucleic acid or the magnetic bead after the nucleic acid is eluted and dissociated will be scattered in the reaction chamber, which on one hand makes the extraction and purification process of nucleic acid to be more convenient and controllable, and on the other hand, the washing and replacement of solid phase material for nucleic acid extraction is more convenient.

(2) For the apparatus of the present invention, a venting element is provided in the waste storage chamber for changing the air pressure between the waste storage chamber and the reaction chamber such that the waste liquid in the reaction chamber is easily discharged; and by reducing air pressure by the venting element, the fluid in the reaction chamber is discharged into the waste storage chamber under the action of negative pressure, which needs not to pressurize the reaction chamber to discharge the liquid, facilitating the experimental operations.

(3) The apparatus and method of the present invention avoid the mixing of reagents caused by repeated microfluidic channels, improve the purity and concentration of the extracted DNA, thereby improving the efficiency of the amplification reaction to achieve smooth and rapid reactions.

(4) The apparatus of the present invention achieves gas and liquid communication between the PCR reaction tube and the PCR reaction solution chamber via the input port and the discharge port, effectively avoids the generation of bubbles during the liquid injection process, and moreover, through observation on the spill of liquid at the discharge port, it can be judged whether the liquid injection is completed.

(5) In the present invention, by using an integrated control system, the conventional manual process of nucleic acid extraction and purification is integrated into a fully automatic closed process, making the operation more conveniently and quickly and improving the efficiency of experimental work.

BRIEF DESCRIPTION OF THE DRAWINGS

FIG. 5A and 5B are a perspective view of a suction column, wherein FIG. 5A is a structural view of a suction column having a gasket, and FIG. 5B is structural view of a suction column without a gasket.

Notes: 1 top cover, 2 shell, 3 rotary disk, 4 base, 5 PCR reaction tube, 6 suction column, 7 piston, 701 recess, 8 protrusion, 9 seal, 10 magnetic bead, 11 permanent magnet, 201 reaction chamber, 2011 receiving chamber, 202 waste storage chamber, 203 lysis chamber, 204 wash chamber, 2041 primary wash chamber, 2042 secondary wash chamber, 2043 tertiary wash chamber, 205 eluent chamber, 206 PCR reaction solution chamber, 2061 Primary PCR reaction solution chamber, 2062 Secondary PCR reaction solution chamber, 207 through hole, 208 input port, 209 discharge port, 210 rib, 211 boss, 301 inlet microfluidic channel, 302 first outlet microfluidic channel, 303 second outlet microfluidic channel, 304 third outlet microfluidic channel, 305 fourth outlet microfluidic channel, 306 opening, 307 boss, 501 first port, 502 second port, 601 gasket, 602 suction column external end, 401 card slot, 402 card slot groove, 901~904 seal through hole, 905 groove.

DETAILED DESCRIPTION

The technical solutions in the embodiments of the present invention are explicitly and completely described in the following with reference to the accompanying drawings, which are only a part of rather than all of the embodiments of the present invention. All other technical solutions obtained by those skilled in the art based on the embodiments of the present invention without creative work fall within the scope of protection of the present invention.

In the present invention, unless otherwise specified and defined, "connected", "fixed, immobilized", etc. should be understood broadly. For example, "fixed, immobilized" may be a fixed connection, or may be a detachable connection, or integrated; may be a direct connection, or an indirect connection through an intermediary, or may be an internal communication of two elements or an interaction relationship of two elements, unless otherwise explicitly defined. For those skilled in the art, the specific meanings of these foregoing terms can be understood on a case-by-case basis in the present invention.

Example 1

Figure 1A:
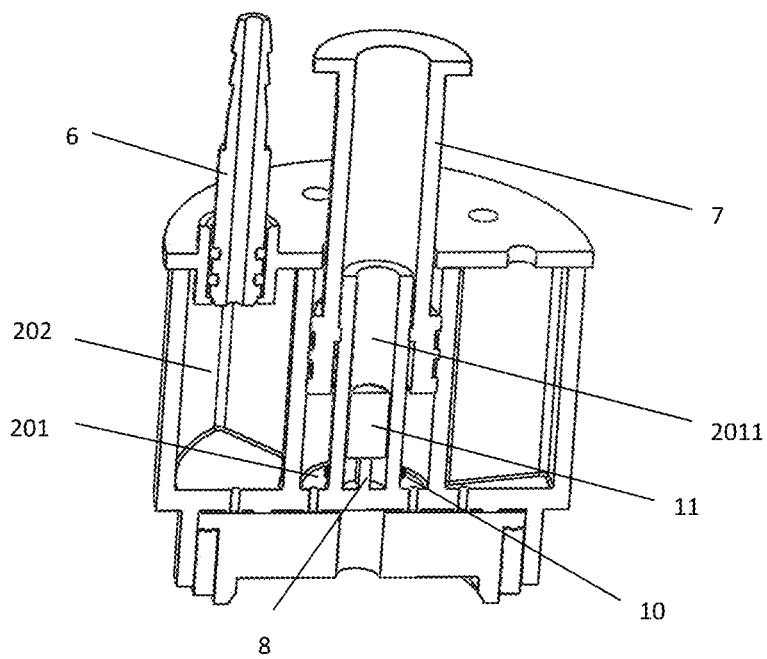
FIG. 1A and 1B are perspective cross-sectional views of a nucleic acid extraction apparatus of the present invention, wherein a partial enlarged view of FIG. 1B is a cross-sectional view of a piston.
Figure 1B:
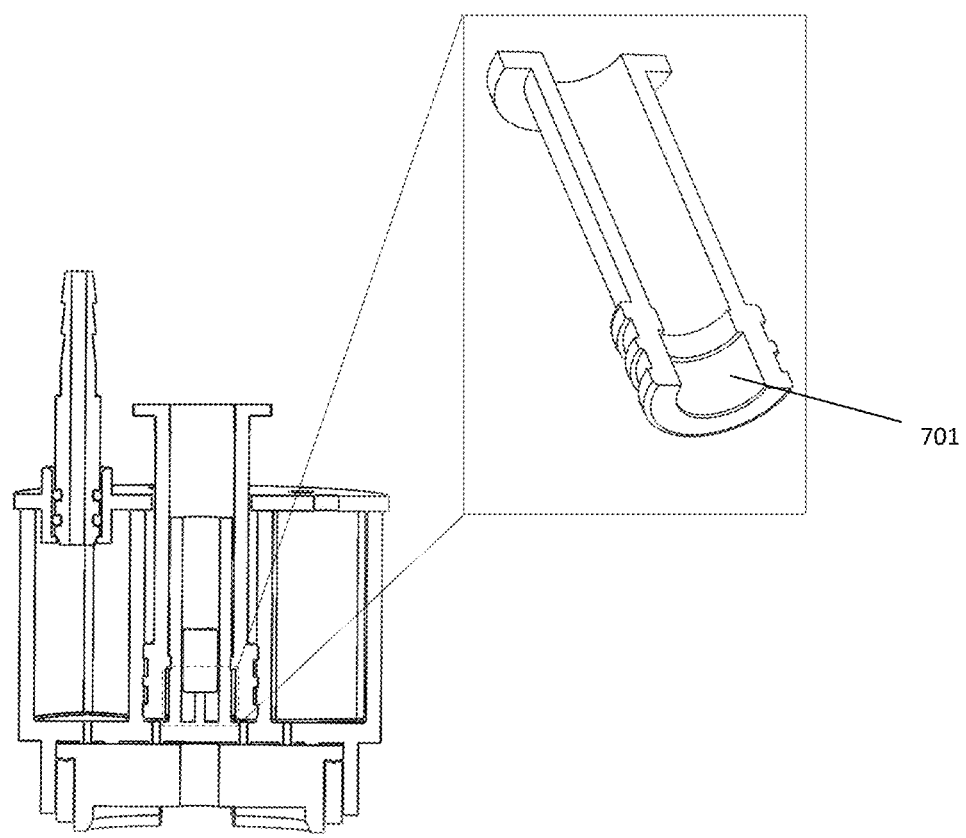
Figure 2:
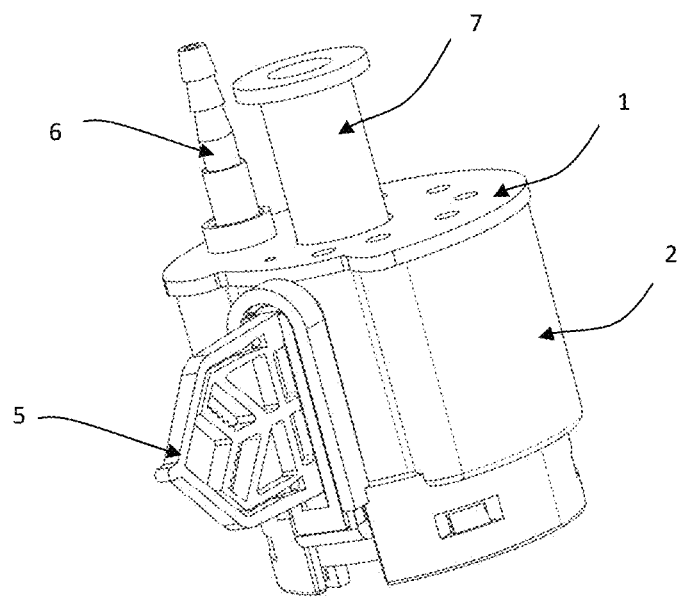
FIG. 2 is a perspective view of a nucleic acid extraction apparatus of the present invention.
Figure 3:
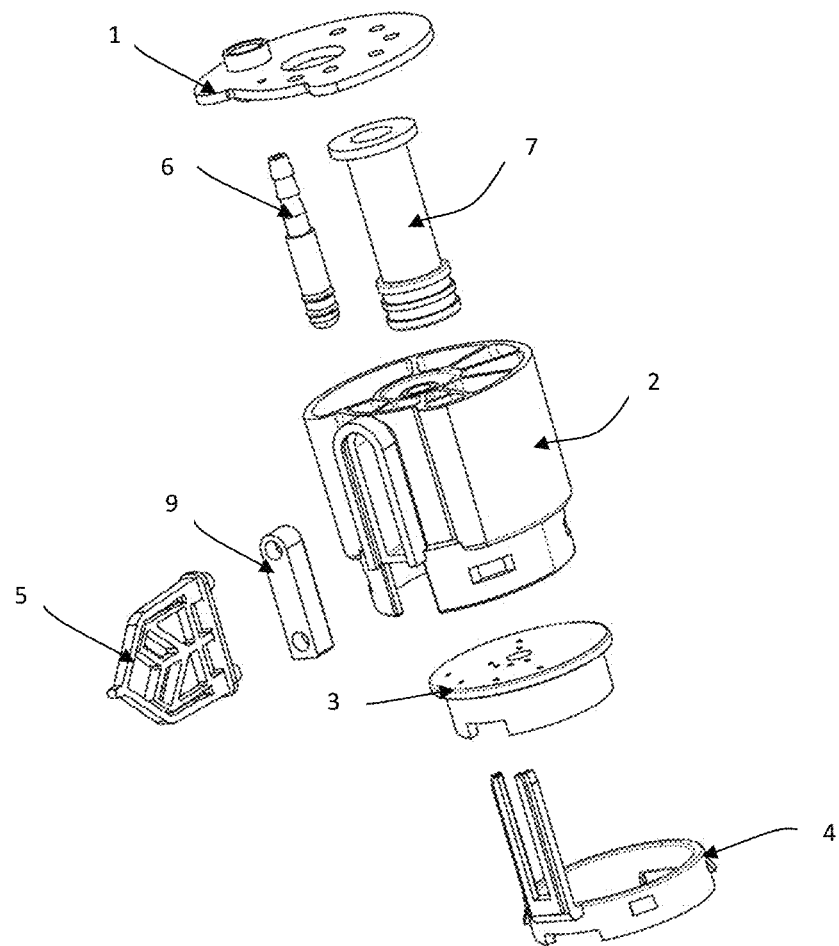
FIG. 3 is an exploded view of the apparatus of FIG. 2.

FIGS. 1-4 show a particular embodiment of a nucleic acid extraction apparatus including a shell having a plurality of chambers. As seen in FIG. 2 and FIG. 3, the nucleic acid extraction apparatus has a top cover 1 and a base 4, and the top cover 1 has openings for injecting samples or reagents into the respective chambers.

FIG. 1 shows a nucleic acid extraction apparatus of the present invention, comprising a nucleic acid extraction element, a waste storage chamber 202 and a reaction chamber 201. The nucleic acid extraction element is used to add or store reagents for nucleic acid extraction and purification, the waste storage chamber 202 is used to store waste liquid generated during the reaction process, and the reaction chamber 201 is a place where nucleic acid is extracted. The nucleic acid extraction element, the waste storage chamber, and reaction chamber are located on the shell 2. In this embodiment, a reaction chamber is selectively in communication with the nucleic acid extraction element and the waste storage chamber, and the apparatus achieves fluid exchange by a pressure change between the waste storage chamber and the reaction chamber.

The term "fluid exchange" as used herein means that a fluid can flow from one place to another, and the flow process may be directed by some physical structures. The term "directed by some physical structures" means that a fluid passively or actively flows to another place by passing through the surface or interior space of these physical structures. The "passively" generally means that the flow is caused by an external force, for example, flow under a pressure. Specifically, in the present invention, it means that a fluid can enter the reaction chamber from the nucleic acid extraction element or enter the nucleic acid extraction element or the waste storage chamber from the reaction chamber, to achieve repetitive switching between these chambers.

The term "selectively" as used herein means that, the waste storage chamber is not in fluidic communication with the reaction chamber when the reaction chamber is in fluidic communication with the nucleic acid extraction element; and the reaction chamber is not in fluidic communication with the nucleic acid extraction element when the waste storage chamber is in fluidic communication with the reaction chamber, that is, the reaction chamber is selectively in fluidic communication with the nucleic acid extraction element or in fluidic communication with the waste storage chamber when appropriate.

Specifically, in one embodiment, a piston 7 is movably placed in the reaction chamber. When the piston moves up along the reaction chamber, the reaction chamber expands in volume, and its pressure decreases, the fluid is sucked into the reaction chamber from the nucleic acid extraction element or the waste storage chamber; when the fluid in the reaction chamber needs to be discharged, the piston moves down along the reaction chamber, the reaction chamber is shrank in volume, and its pressure increases, the fluid is pressed into the nucleic acid extraction element or the waste storage chamber from the reaction chamber.

In a preferred embodiment, the fluid flows from the reaction chamber to the waste storage chamber under a negative pressure by reducing the air pressure in the waste storage chamber rather than pressurizing the reaction chamber by a piston. In this embodiment, the negative pressure drives the fluid from the reaction chamber into the waste storage chamber, and the piston moves downward along the reaction chamber under the negative pressure to prepare for the generation of negative pressure in the reaction chamber.

In some specific circumstances, for example, in order to further mix the fluid evenly, by reducing the pressure of the waste storage chamber, the fluid flows from the reaction chamber into the waste storage chamber under the negative pressure, and then by reducing the pressure of the reaction chamber, the fluid flows from the waste storage chamber into the reaction chamber under the negative pressure, by repeating this process, the fluid is repeatedly exchanged between the two chambers to mix well. Wherein, the negative pressure of the reaction chamber is generated by the upward movement of the piston.

Figures 5A, 5B:
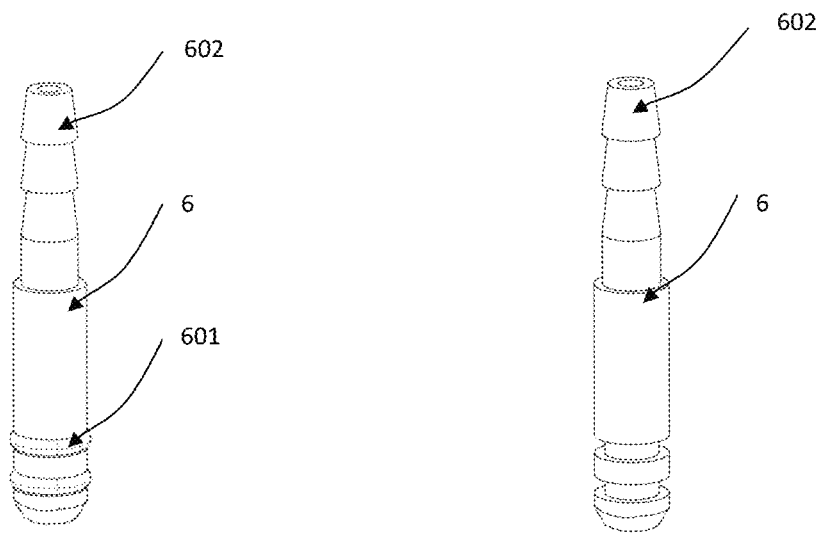

In a preferred embodiment, as shown in FIG. 1, the air pressure in the waste storage chamber is reduced via a venting element that is in communication with the waste storage chamber. Preferably, the venting element is a columnar suction column that communicates with the waste storage chamber, more preferably it is a cylindrical suction column 6. As shown in FIG. 5A and 5B, the suction column 6 is a hollow cylinder having one end communicated with the waste storage chamber 202. In a preferred embodiment, a gasket 601 is provided at the junction of the suction column and the waste storage chamber 202 to improve the sealing of the suction column and the waste storage chamber, and the gasket is preferably an elastic material. The other end of the suction column is exposed outside the nucleic acid extraction apparatus for connection to an air pumping device, preferably, the suction column external end 602 is connected to the air pumping device via a hose. The air pumping device described herein is preferably a vacuum pump or a negative pressure pump that reduces the air pressure in the waste storage chamber 202 by evacuating the waste storage chamber 202. As the air pressure of the waste storage chamber 202 decreases, the fluid in the reaction chamber 201 enters the waste storage chamber 202, at this time, the fluid can be discharged from the reaction chamber 201 into the waste storage chamber 202 without pressurizing the reaction chamber 201, which is easy to operate and labor-saving. In a specific embodiment, the piston 7 connected to the reaction chamber 201 moves downward relative to the reaction chamber as the liquid in the reaction chamber is discharged. The apparatus of this embodiment not only facilitates the discharge of waste liquid from the reaction chamber 201 to the waste storage chamber 202, but also is more suitable for the treatment of biological samples having certain infectivity or toxicity. Because the suction column 6 is directly connected to the air pumping device during the process of nucleic acid extraction, the liquid flow can be achieved by vacuum pumping, and no waste gas will be discharged from the waste storage chamber 202.

In a preferred embodiment, a solid phase material for nucleic acid extraction is provided in the reaction chamber 201 for capturing target nucleic acids in the samples. In a preferred embodiment, the solid phase material for nucleic acid extraction is a magnetic bead 10. When the solid phase material for nucleic acid extraction is a magnetic bead, the reaction chamber has a permanent magnet 11 inside so that the magnetic bead is fixed in the reaction chamber. In a preferred embodiment, the reaction chamber 201 is a cylindrical chamber, and a hollow receiving chamber 2011 for accommodating the permanent magnet 11 is disposed in the center of the reaction chamber, and the receiving chamber 2011 is also a cylindrical chamber, the permanent magnet 11 is disposed in the hollow receiving chamber 2011. When the permanent magnet is placed in the receiving chamber 2011, the magnetic bead 10 is fixed on the outer sidewall of the receiving chamber 2011 by the adsorption of the permanent magnet 11 (as shown in FIG. 1A). In a preferred embodiment, the bottom of the receiving chamber 2011 has a protrusion 8, and a permanent magnet 11 is placed on the protrusion 8. The setting of the protrusion 8 enables the permanent magnet 11 to be disposed at an appropriate height, thereby ensuring that the magnetic bead 10 is adsorbed in an appropriate position on the sidewall of the receiving chamber 2011 rather than close to the bottom of the reaction chamber. In a preferred embodiment, the piston 7 is a hollow piston having a cylindrical shape. When the piston is placed in the reaction chamber 201, it can be moved up and down along the reaction chamber or up and down along the receiving chamber 2011. In a preferred embodiment, a recess 701 is provided on the sidewall at the bottom of the piston 7, that is, the sidewall at the bottom of the piston protrudes outwardly to form a recess 701, and the recess 701 and the sidewall at the bottom of the receiving chamber 2011 form a space for accommodating the magnetic bead, as shown in the dotted line box of FIG. 1B. The magnetic bead binds to free DNAs in the samples specifically to form a magnetic bead-DNA complex, thereby immobilizing DNAs at a specific position in the reaction chamber.

The samples include at least one of the following: cells, spores, microorganisms, biological tissues, biological fluids or environmental samples, etc.

In a preferred embodiment, the nucleic acid extraction element comprises: a lysis chamber 203 for adding and storing a mixture of sample and lysate; a wash chamber 204 for adding and storing washing liquid; an eluent chamber 205 for adding and storing eluent; the reaction chamber 201 is sequentially in communication with the lysis chamber 203, the wash chamber 204, and the eluent chamber 205 to extract and purify nucleic acids in the samples.

The lysate includes at least one of the following: guanidine hydrochloride, chaotropic salt, erythrocyte lysis reagent, chelating agent, sodium hydroxide, DNase inhibitor, RNase inhibitor, anticoagulant, coagulant, protease, surfactant, etc.; the washing liquid includes at least one of the following: ethanol, sodium chloride, Tris hydrochloric acid, etc.; the eluent is sterile deionized water or Tris hydrochloric acid. The specific flow is as follows: (1) the lysis chamber 203 is in communication with the reaction chamber 201, and samples and lysate enter the reaction chamber 201 for the lytic reaction, during the process, one the one hand, an additional device such as a sonic vibrator can be connected to the apparatus of the present invention to facilitate the lysis of samples; and on the other hand, after the mixture of lysate and samples enters the reaction chamber 201, the reaction chamber 201 is in communication with the waste storage chamber 202, and the mixture of lysate and samples are exchanged repeatedly between the reaction chamber and the waste storage chamber by changing the pressure between the reaction chamber and the waste storage chamber, to facilitate the complete lysis of samples; (2) After the completion of the lytic reaction, the nucleic acids in the sample are bound to the magnetic bead 10 and immobilized in the reaction chamber 201, and the lytic waste liquid enters the waste storage chamber 202; (3) the wash chamber 204 is in communication with the reaction chamber 201, and washing liquid enters the reaction chamber 201, such that the magnetic bead that has been bound to the nucleic acid is immersed in the washing liquid to clean and remove the impurities. During the process, on the one hand, the sound wave can be used to promote the mixing, and on the other hand, the washing liquid can be exchanged repeatedly between the reaction chamber 201 and the wash chamber 204 by moving up and down the piston, to ensure thorough washing; (4) the reaction chamber 201 is in communication with the waste storage chamber 202, the waste storage chamber 202 is decompressed, the waste liquid is discharged into the waste storage chamber 202, and the nucleic acid is bound to the magnetic bead and immobilized in the reaction chamber 201, and the washing process can be repeated several times according to the actual situation; (5) the eluent chamber 205 is in communication with the reaction chamber 201, the eluent enters the reaction chamber 201, so that the magnetic bead bound to nucleic acids is immersed in the eluent, the nucleic acid is separated from the magnetic bead and dissolved in the eluent. In the process, the sound wave vibration can be used to facilitate mixing and accelerate the elution, or the eluent can be repeatedly exchanged between the reaction chamber 201 and eluent chamber 205 by moving up and down the piston, to ensure thorough elution.

In a preferred embodiment, after the nucleic acid is detached from the magnetic bead, the extraction of the nucleic acid in the sample is completed, at this time, the magnetic bead can be washed for the next time of extraction of nucleic acids, that is, the apparatus of the present invention can be repeatedly used for multiple times, to save experimental costs.

Figure 4:
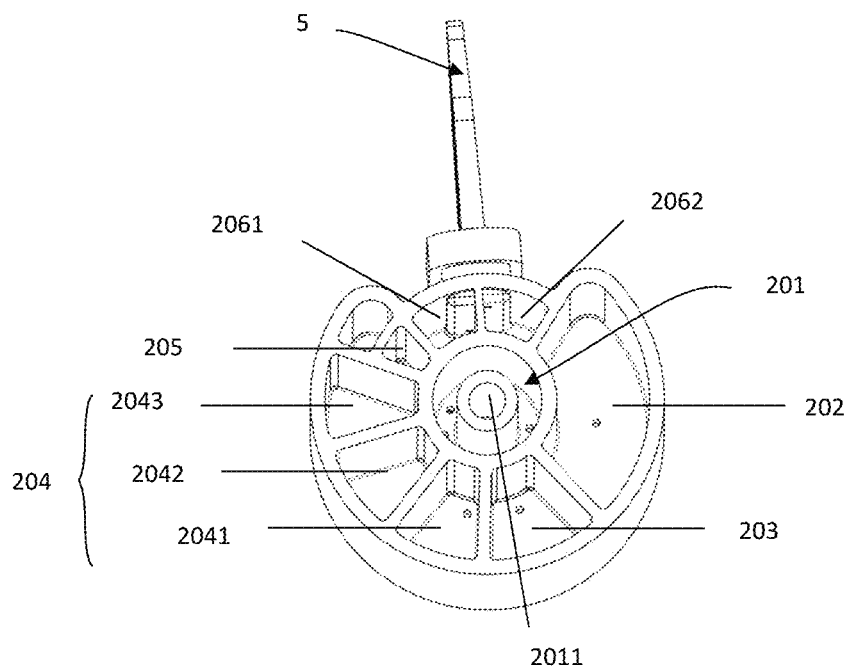
FIG. 4 is another perspective view of a nucleic acid extraction apparatus of the present invention.

In a preferred embodiment, as shown in FIG. 4, the wash chamber 204 comprises a primary wash chamber 2041, a secondary wash chamber 2042 and a tertiary wash chamber 2043. The primary wash chamber 2041, the secondary wash chamber 2042, and the tertiary wash chamber 2043 are sequentially in communication with the reaction chamber 201, respectively. It is to be understood that the apparatus described herein may comprise a plurality of wash chambers, for example, two, three, four, etc., to satisfy nucleic acid purification using a plurality of different washing liquids, or to use a larger amount of the same washing liquid to perform washing, to improve the purity of nucleic acids.

Figure 6:
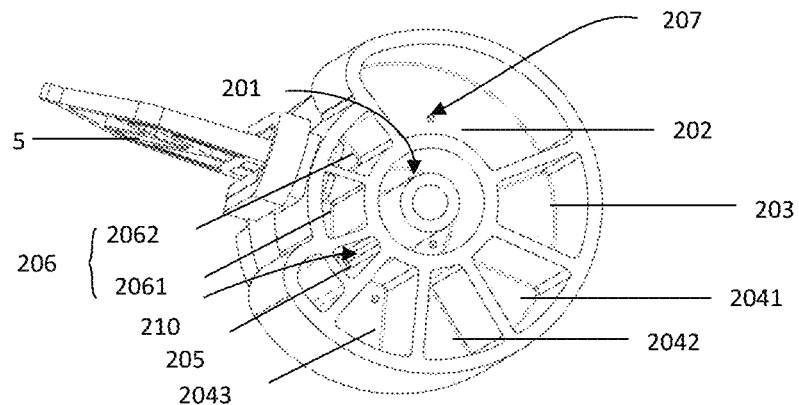
FIG. 6 is another perspective view of a nucleic acid extraction apparatus of the present invention.

In a preferred embodiment, the lysis chamber 203, the wash chamber 204, the eluent chamber 205 and the waste storage chamber 202 are sequentially in communication with the reaction chamber 201 through a plurality of mutually independent microfluidic channels, respectively. As shown in FIG. 3, FIG. 4, and FIG. 6, the lysis chamber 203, the wash chamber 204, the eluent chamber 205, the waste storage chamber 202 and the reaction chamber 201 are disposed in a cylindrical shell 2, wherein the reaction chamber 201 is disposed in the center of inner circle of a cylindrical shell, and the lysis chamber 203, the wash chamber 204, the eluent chamber 205 and the waste storage chamber 202 are distributed on the outer circle of the cylindrical shell along the circumference of the reaction chamber 201, and are radially connected to the reaction chamber 201; the plurality of mutually independent microfluidic channels are disposed on a rotary disk 3, and the rotary disk is composed of two parts; the shell 2 including the plurality of chambers is connected to the rotary disk 3, and the rotation of the rotary disk 3 enables the reaction chamber 201 to pass through the plurality of microfluidic channels to achieve fluidic communication with the lysis chamber 203, the wash chamber 204, the eluent chamber 205 or the waste storage chamber 202 in sequence.

Figure 7:
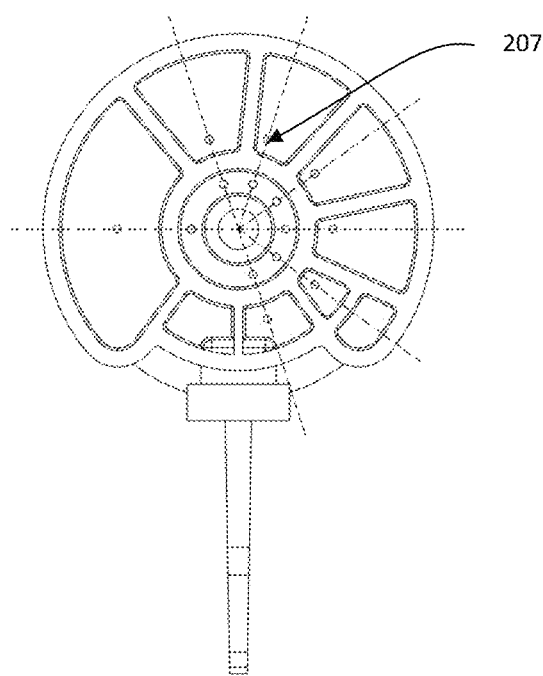
FIG. 7 is a top view of a nucleic acid extraction apparatus of the present invention.

As shown from FIG. 4, FIG. 6 and FIG. 7, the bottoms of the lysis chamber 203, the wash chamber 204, the eluent chamber 205 and the waste storage chamber 202 are provided with a through hole 207 respectively, and the bottom of the reaction chamber 201 is provided with a plurality of through holes 207 corresponding to the through hole 207 at the bottoms of the above chambers one to one respectively. Through the one-to-one corresponding two through holes 207, the lysis chamber 203, the wash chamber 204, the eluent chamber 205, the waste storage chamber 202 are in communication with the reaction chamber. As shown from FIG. 7, the distances between two through holes that communicate the lysis chamber 203 with the reaction chamber 201, communicate the primary wash chamber 2041 with the reaction chamber 201, communicate the secondary wash chamber 2042 with the reaction chamber 201, communicate the tertiary wash chamber 2043 with the reaction chamber 201, communicate the eluent chamber 205 with the reaction chamber 201 are equal, and these through holes are distributed with equal distance from the center of the reaction chamber. The distance between the two through holes that communicate the waste storage chamber 202 with the reaction chamber 201 is different from the distance between the two through holes that communicate the above chambers and the reaction chamber.

Figure 9A:
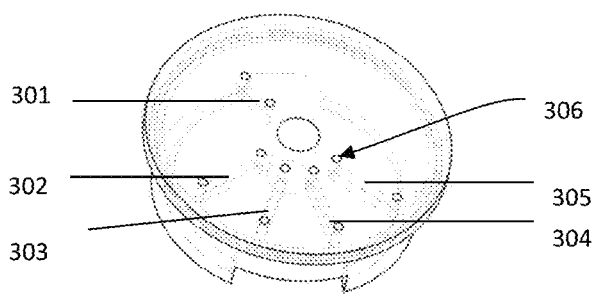
FIG. 9A and 9B are a perspective view and a front view of a rotary disk of a nucleic acid extraction apparatus of the present invention.
Figure 9B:
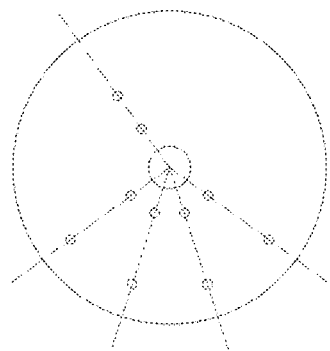
Figure 10:
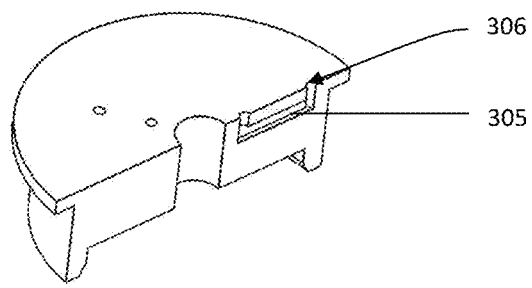
FIG. 10 is a cross-sectional view of a rotary disk of a nucleic acid extraction apparatus of the present invention.

FIG. 9 shows that a plurality of radially-extending independent microfluidic channels are distributed on the rotary disk, wherein each microfluidic channel has two opening 306 on the outer surface of the rotary disk, and the two opening 306 are respectively corresponding to the two through holes 207 that communicate the lysis chamber with the reaction chamber, communicate the wash chamber with the reaction chamber, communicate the eluent chamber with the reaction chamber and communicate the waste storage chamber with the reaction chamber. When the rotary disk is rotated horizontally by a certain angle, two openings 306 of a microfluidic channel are engaged with the two through holes 207 on the shell, to achieve fluidic communication between the above chambers and the reaction chamber. The microfluidic channel includes an inlet microfluidic channel 301 and a plurality of outlet microfluidic channels. In a preferred embodiment, there are four outlet microfluidic channels, which are respectively named as a first outlet microfluidic channel 302, a second outlet microfluidic channel 303, a third outlet microfluidic channel and a fourth outlet microfluidic channel 305. The outlet microfluidic channels 302, 303, 304, and 305 have the same length, but they differ from the inlet microfluidic channel 301 in length. It is to be understood that the number of outlet microfluidic channels can be set according to the number of times that the waste liquid needs to be discharged.

In a preferred embodiment, the length of the inlet microfluidic channel 301 is equal to the distance between two through holes that communicate the lysis chamber 203 with the reaction chamber 201, communicate the primary wash chamber 2041 with the reaction chamber 201, communicate the secondary wash chamber 2042 with the reaction chamber 201, communicate the tertiary wash chamber 2043 with the reaction chamber 201 and, communicate the eluent chamber 205 with the reaction chamber 201. The length of the outlet microfluidic channels 302, 303, 304, 305 is equal to the distance between the two through holes that communicate the waste storage chamber 202 with the reaction chamber 201. Through the rotation of the rotary disk, the one inlet microfluidic channel 301 makes the lysis chamber 203, the primary wash chamber 2041, the secondary wash chamber 2042, the tertiary wash chamber 2043 and the eluent chamber 205 to be in communication with the reaction chamber 201 sequentially, while the waste storage chamber 202 is in communication with the reaction chamber 201 sequentially via the outlet microfluidic channels 302, 303, 304, 305.

In a preferred embodiment, five groups of through holes that that communicate the lysis chamber 203 with the reaction chamber 201, communicate the primary wash chamber 2041 with the reaction chamber 201, communicate the secondary wash chamber 2042 with the reaction chamber 201, communicate the tertiary wash chamber 2043 with the reaction chamber 201 and, communicate the eluent chamber 205 with the reaction chamber 201 are equidistantly distributed around the center of the reaction chamber 201, that is, the radial extension lines of the five groups of through holes intersect at the center of the reaction chamber, and the angles formed by the radial extension lines of the five groups of through holes are equal, preferably the angle is 36 degrees (as shown in FIG. 7).

The foregoing microfluidic channels are radially distributed with the center of the rotary disk 3 as a center of a circle, wherein the radial extension lines of the outlet microfluidic channels 302, 303, 304, and 305 intersect at the center of the rotary disk 3, and the angles formed between the radially-extending lines are equal, preferably 36 degrees, wherein the center of the reaction chamber of the apparatus is overlapped with the center of the rotary disk.

Figure 8:
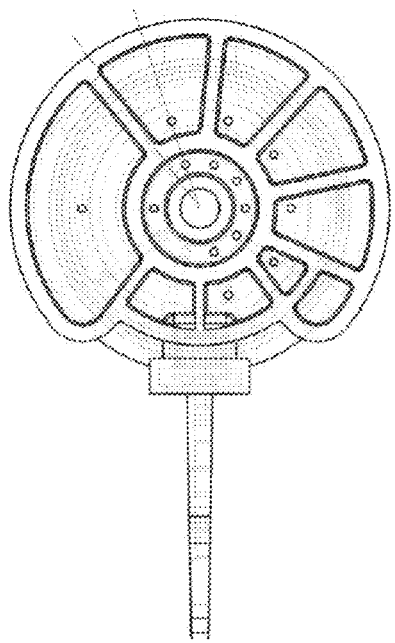
FIG. 8 is another top view of a nucleic acid extraction apparatus of the present invention.

When the nucleic acid extraction apparatus is in a non-fluidic communication state (FIG. 8), the angle between the radial extension line of the inlet microfluidic channel 301 and the radial extension line of the two through holes that communicate the lysis chamber 203 and the reaction chamber 201 is 18 degrees. By horizontally rotating the rotary disk 18 degrees clockwise relative to the lysis chamber 203, the lysis chamber 203 can be in communication with the reaction chamber 201 via the inlet microfluidic channel 301. By further horizontally rotating the rotary disk clockwise, the waste storage chamber 202, the wash chamber 204 or the eluent chamber 205 are in fluidic communication with the reaction chamber 201 sequentially.

In a preferred embodiment, the nucleic acid extraction apparatus further comprises a nucleic acid amplification element, and the nucleic acid amplification element comprises a PCR reaction solution chamber 206 that is in communication with the reaction chamber, inside of which is provided with reagents for a PCR reaction.

The PCR reaction reagents include at least one of the following: Bst polymerase, Taq polymerase, reverse transcriptase, dNTPs, primers, probes, and the PCR reaction reagent is preferably a liquid.

In a preferred embodiment, as shown in FIG. 6, the PCR reaction solution chamber 206 includes a primary PCR reaction solution chamber 2061 and a secondary PCR reaction solution chamber 2062, which are independent of each other. The primary PCR reaction solution chamber 2061 is in communication with the reaction chamber 201 via the inlet microfluidic channel 301, and the nucleic acids are eluted and dissolved in the eluent, at this time, the reaction chamber 201 is in communication with the primary PCR reaction solution chamber 2061 to further move the piston upward, and the PCR reaction solution enters the reaction chamber 201 to mix with nucleic acids. Further, the PCR reaction solution and the nucleic acids can be sufficiently mixed by sound wave oscillation. In this process, it is necessary to ensure that some of air is inhaled in the PCR reaction solution. The purpose of air inhalation is to ensure that the PCR reaction solution enters the reaction chamber 201 in whole.

In a preferred embodiment, the nucleic acid amplification element further comprises a PCR reaction tube 5 connected to the PCR reaction solution chamber 206. The entire PCR reaction and the corresponding optical result detection are completed in a PCR reaction tube 5. The PCR reaction tube 5 can be directly placed in a temperature control instrument for PCR amplification reaction or can be removed from a nucleic acid amplification device and placed in a temperature control instrument for amplification reaction.

Figure 11:
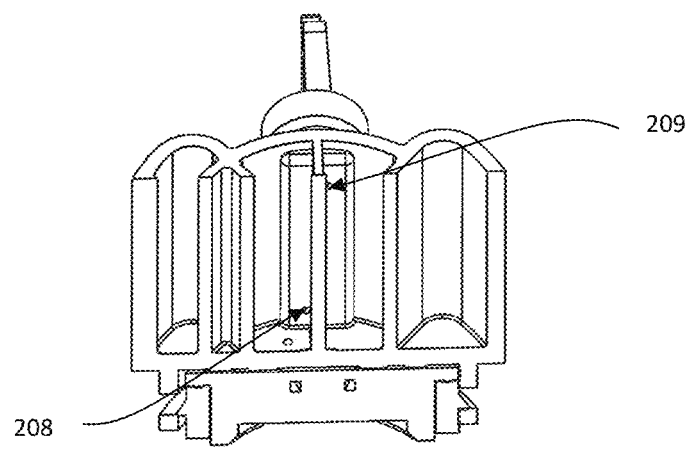
FIG. 11 is a cross-sectional view of a PCR reaction solution chamber of a nucleic acid extraction apparatus of the present invention.
Figure 12:
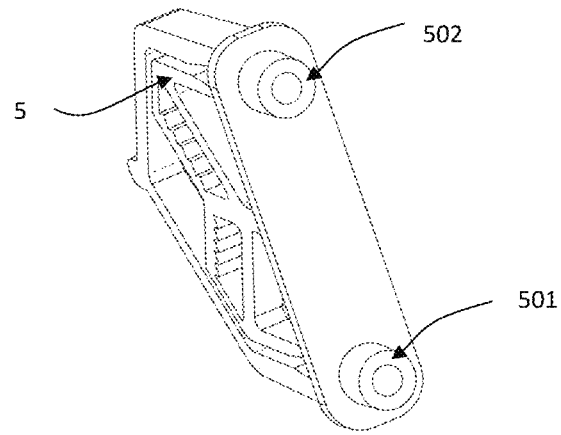
FIG. 12 is a structural diagram of a PCR reaction tube of a nucleic acid extraction apparatus of the present invention.

In a preferred embodiment, an input port 208 is provided at the bottom of the sidewall of the primary PCR reaction solution chamber 2061, and the input port 208 is disposed on a sidewall having a certain height difference from the bottom of the primary PCR reaction solution chamber 2061. A discharge port 209 is provided at the top of the sidewall of the secondary PCR reaction solution chamber (FIG. 11), and the height of the discharge port 209 from the bottom of the chamber is higher than the height of the input port 208 from the bottom of the chamber. Both the input port 208 and the discharge port 209 are through holes, and the input port 208 and the discharge port 209 correspond to the first port 501 and the second port 502 (FIG. 12) of the PCR reaction tube injection channel, respectively. The PCR reaction tube is in fluidic and gaseous communication with the PCR reaction solution chamber through the input port 208, the discharge port 209, the first port 501 and the second port 502 described above.

The piston 7 moves downward to pressurize the reaction chamber 201, and the mixture of the PCR reaction solution and the nucleic acids enters the PCR reaction solution chamber 206 from the reaction chamber 201 via the inlet microfluidic channel 301. When the liquid level of the mixed solution in the PCR reaction solution chamber 206 exceeds the input port 208, the air at the top of the PCR reaction solution chamber 206 begins to compress, causing the mixed solution to enter the PCR reaction tube 5 from the input port 208. As the liquid enters, the air in the PCR reaction tube 5 is discharged from the discharge port 209, such that the liquid can enter the PCR reaction tube smoothly.

The discharge port has the following two functions: first, to evacuate the air in the PCR reaction tube 5, to facilitate the entry of liquid into the PCR reaction tube 5; second, to indicate whether the liquid is sufficiently filled with the PCR reaction tube 5, and when there is liquid spill from the discharge port 209, it indicates that the mixed solution is completely filled in the PCR reaction tube 5.

In a preferred embodiment, the input port 208 and the discharge port 209 are two small holes having a pore size less than that of the first port 501 and the second port 502 of the PCR reaction tube. By pressurizing the reaction chamber 201, the mixed solution is pressed into the PCR reaction tube from the input port 208. This structure used can effectively avoid the generation of bubbles in the mixed solution injected into the PCR reaction tube or facilitate the discharge of bubbles, to prevent introduction of bubbles in the mixed solution that may interfere with the PCR reaction results.

Figure 14A:
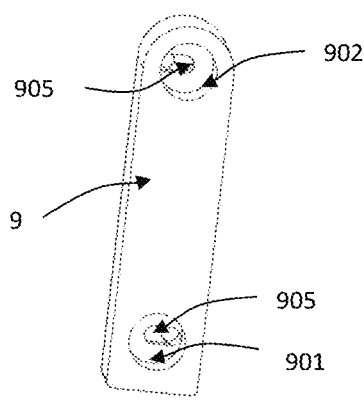
FIG. 14A is a front view and FIG. 14B is a rear view of a seal.
Figure 14B:
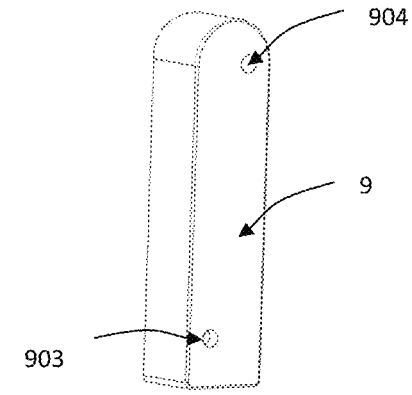

In a preferred embodiment, a seal 9 is provided at the junction of the PCR reaction tube 5 and the PCR reaction solution chamber 206, preferably the seal 9 is made of an elastic material such as a silica gel. As shown in FIGS. 14A and 14B, seal 9 is a rectangular columnar structure, with the upper and lower through holes penetrating the cylinder. Wherein, one side of the seal 9 is used for connection with the PCR reaction tube 5, and the other side is used for connection with the PCR reaction solution chamber 206. The two through holes 901 and 902 on the connection surface of the PCR reaction tube 5 correspond to the first port 501 and the second port 502 of the PCR reaction tube 5, respectively, and the pore size thereof corresponds to the first port 501 and the second port 502 of the PCR reaction tube. The first port 501 and the second port 502 of the PCR reaction tube 5 are inserted into the through holes 901 and 902, respectively and are in interference fit with the seal 9. The two through holes 903 and 904 on the connection surface of the PCR reaction solution chamber 206 correspond to the input port 208 and the discharge port 209 of the PCR reaction solution chamber 206 respectively, and the pore size thereof corresponds to the input port 208 and the discharge port 209. Further, there is a groove 905 at the junction of the through holes 901 and 903 or through holes 902 and 904, and the groove 905 makes the input port 208 and the first port 501, or the discharge port 209 and the second port 502 in a straight line. The fluid enters from the through hole 903, flows through the groove 905 and the first port 501, and then enters the injection channel of the PCR reaction tube 5, thereby entering the PCR reaction tube 5.

In a preferred embodiment, a sponge-like non-absorbent material capable of slowly leaking gas is provided at the top of the primary PCR reaction solution chamber 2061, preferably the material is high-density hydrophobic cotton. The high density hydrophobic cotton is set to achieve slow pumping of air, so that the air pressure of the primary PCR reaction solution chamber 2061 is kept consistent with that of the secondary PCR reaction solution chamber 2062, to prevent the mixed solution from flowing in the primary PCR reaction solution chamber 2061 and avoid the generation of bubbles in the fluid. Specifically, the piston moves downward to pressurize the reaction chamber 201, and the mixed solution of the nucleic acids and the PCR reaction solution enters the primary PCR reaction solution chamber 2061 from the reaction chamber 201 via the inlet microfluidic channel 302, and the liquid level in the primary PCR reaction solution chamber 2061 continuously rises, and when the liquid level is higher than the height of the input port, the primary PCR reaction solution chamber 2061 starts to be pressurized. At this time, the air pressure of the secondary PCR reaction solution chamber 2062 is atmospheric pressure. By setting the high density hydrophobic cotton on the top of the primary PCR reaction solution chamber 2061, the primary PCR reaction solution chamber 2061 can achieve slow venting such that the air pressure of the primary PCR reaction solution chamber 2061 is consistent with the secondary PCR reaction solution chamber 2062, making it easier for the liquid to enter the PCR reaction tube 5. In a preferred embodiment, the venting time of the high density hydrophobic cotton is set to 5 to 10 seconds. Preferably, the high density hydrophobic cotton is filled at ⅓ of the height of the body of the primary PCR reaction solution chamber 2061, for example, fixedly filled at the top of the primary PCR reaction solution chamber in a form of plunger piston. The high-density hydrophobic cotton does not absorb water and does not absorb the PCR reaction solution, so that it will not produce any influence on the nucleic acid extraction process.

In a preferred embodiment, as shown in FIG. 6, a rib 210 is disposed on the wall of the eluent chamber 205 for reducing the amount of eluent used.

Figure 13:
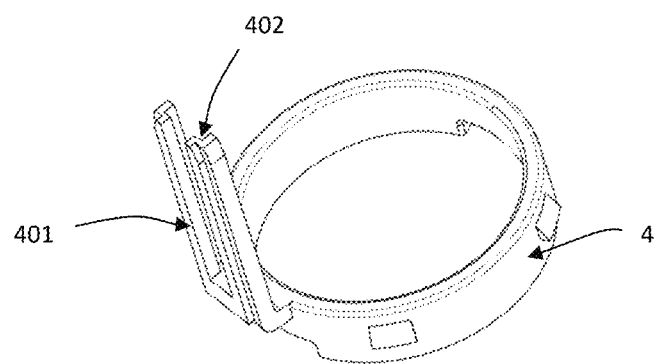
FIG. 13 is a perspective view of a base of a nucleic acid extraction apparatus of the present invention.

In a preferred embodiment, as shown in FIG. 13, a card slot 401 for fixing the PCR reaction tube 5 is provided on the base 4 of the apparatus of the present invention, and the card slot 401 is integrally formed with the base 4, and the card slot 401 is perpendicular to the base 4, and when the shell 2 is fixed on the base 4, the card slot 401 is in contact with and longitudinally parallel to the shell 2. Specifically, the card slot 401 is fixedly connected to the outer wall of the PCR reaction solution chamber 206. The left and right sides of the card slot 401 are provided with grooves 402 for accommodating a PCR reaction tube, and the PCR reaction tube 5 is inserted and fixed in the groove 402 of the card slot 401, such that the PCR reaction tube 5 and the shell 2 are detachably connected.

Figure 15:
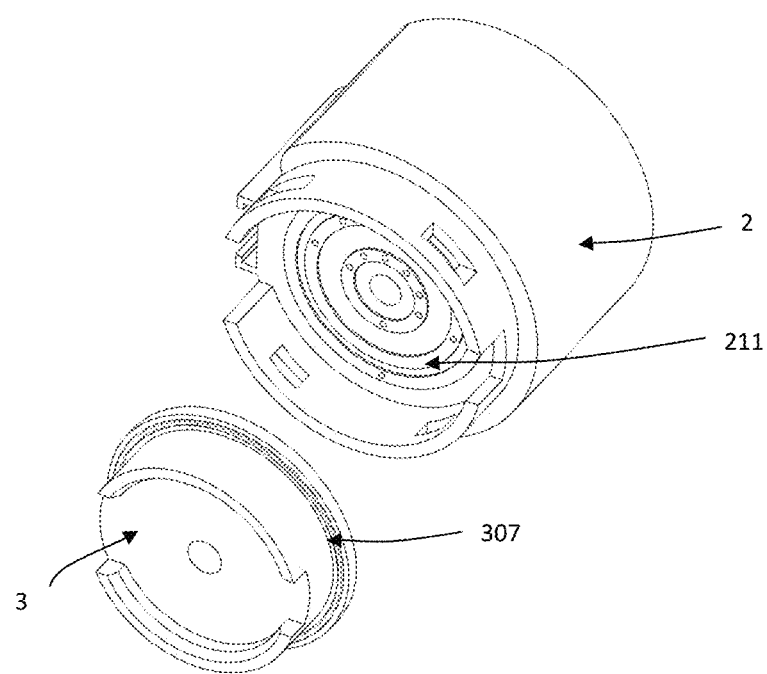
FIG. 15 is a structural diagram of a shell and a rotary disk of a nucleic acid extraction apparatus of the present invention.

In a preferred embodiment, as shown in FIG. 15, a boss 211 is disposed at the connection portion of the bottom of the shell 2 and the rotary disk 3, to enhance the sealing effect of the shell 2 and the rotary disk 3; and a boss 307 is provided at the connection portion of the rotary disk 3 and the base 4, to reduce the friction when the rotary disk rotates.

Figure 16:
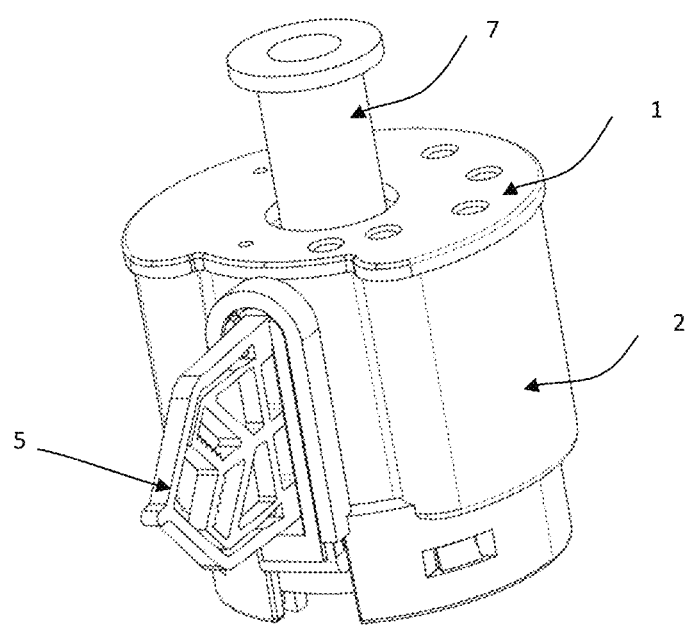
FIG. 16 is a perspective view of a nucleic acid extraction apparatus according to another embodiment of the present invention.

FIG. 16 shows a schematic structural view of another embodiment of a nucleic acid extraction apparatus of the present invention. In this embodiment, a suction column 6 is not provided in the waste storage chamber 202. In this embodiment, by moving the piston 7 upwardly and downwardly, the liquid exchange between the reaction chamber 201 and the lysis chamber 203, between the reaction chamber 201 and the wash chamber 204, between the reaction chamber 201 and the eluent chamber 205, between the reaction chamber 201 and the waste storage chamber 202, the reaction chamber 201 and the PCR reaction solution chamber 206 can be achieved. Specifically, when moving the piston 7 upwardly, the pressure of the reaction chamber 201 decreases, the liquid is sucked into the reaction chamber 201, and when moving the piston 7 downwardly, the pressure of the reaction chamber 201 increases, and the liquid is discharged into the reaction chamber 201. In this embodiment, an aperture is provided at the top cover 1 of the corresponding waste storage chamber 202, and the aperture can ensure that liquid can be smoothly forced from the reaction chamber 201 into the waste storage chamber 202 when the reaction chamber 201 is pressurized. The nucleic acid extraction apparatus of this embodiment is particularly suitable for extraction of nucleic acids from highly safe biological samples.

Example 2

In this embodiment, a method for extraction of nucleic acids using the nucleic acid extraction apparatus described in the Example 1 is described.

Step 1: Open the lysis chamber 203, add a liquid sample, and mix the sample with lysate;

Step 2: rotate the rotary disk 3 horizontally by 18 degrees clockwise, so that the lysis chamber 203 communicates with the reaction chamber 201 via the inlet microfluidic channel 301. Apply an external force to push the reaction chamber piston 7 upward, so that the mixed solution of the lysate and the sample enters the reaction chamber 201, and after lysis of samples, the released nucleic acids bind to the magnetic bead 10 in the reaction chamber;

Step 3: rotate the rotary disk 3 horizontally by 18 degrees clockwise, so that the waste storage chamber 202 communicates with the reaction chamber 201 via the first outlet microfluidic channel 302. Connect the vacuum pump to the suction column 6 for evacuation, and the lytic waste liquid enters the waste storage chamber 202, the magnetic beads bound to nucleic acids are immobilized in the reaction chamber 201;

Step 4: rotate the rotary disk 3 horizontally by 18 degrees clockwise, so that the primary wash chamber 2041 communicates with the reaction chamber 201 via the inlet microfluidic channel 301. Apply an external force to push the reaction chamber piston 7 upward, and the washing liquid enters the reaction chamber 201, such that the magnetic beads bound to nucleic acids are immersed into the washing liquid, to wash and remove impurities;

Step 5: rotate the rotary disk 3 horizontally by 18 degrees clockwise, so that the waste storage chamber 202 communicates with the reaction chamber 201 via the second outlet microfluidic channel 303. Connect the vacuum pump to the suction column 6 for evacuation, and the washing waste liquid enters the waste storage chamber 202, the magnetic beads bound to nucleic acids are immobilized in the reaction chamber 201;

Step 6: rotate the rotary disk 3 horizontally by 18 degrees clockwise, so that the secondary wash chamber 2042 communicates with the reaction chamber 201 via the inlet microfluidic channel 301. Apply an external force to push the reaction chamber piston 7 upward, and the washing liquid enters the reaction chamber 201, such that the magnetic beads bound to nucleic acids are immersed into the washing liquid, to wash and remove impurities;

Step 7: rotate the rotary disk 3 horizontally by 18 degrees clockwise, so that the waste storage chamber 202 communicates with the reaction chamber 201 via the third outlet microfluidic channel 304. Connect the vacuum pump to the suction column 6 for evacuation, and the washing waste liquid enters the waste storage chamber 202, the magnetic beads bound to nucleic acids are immobilized in the reaction chamber 201;

Step 8: rotate the rotary disk 3 horizontally by 18 degrees clockwise, so that the tertiary wash chamber 2043 communicates with the reaction chamber 201 via the inlet microfluidic channel 301. Apply an external force to push the reaction chamber piston 7 upward, and the washing liquid enters the reaction chamber 201, such that the magnetic beads bound to nucleic acids are immersed into the washing liquid, to wash and remove impurities;

Step 9: rotate the rotary disk 3 horizontally by 18 degrees clockwise, so that the waste storage chamber 202 communicates with the reaction chamber 201 via the fourth outlet microfluidic channel 305. Connect the vacuum pump to the suction column 6 for evacuation, and the washing waste liquid enters the waste storage chamber 202, the magnetic beads bound to nucleic acids are immobilized in the reaction chamber 201;

Step 10: rotate the rotary disk 3 horizontally by 18 degrees clockwise, so that the eluent chamber 205 communicates with the reaction chamber 201 via the inlet microfluidic channel 301. Apply an external force to push the reaction chamber piston 7 upward, and the eluent enters the reaction chamber 201, such that the magnetic beads bound to nucleic acids are immersed into the eluent, and the nucleic acids are detached from the magnetic beads and dissolved in the eluent;

Step 11: rotate the rotary disk 3 horizontally by 36 degrees clockwise, so that the primary PCR reaction solution chamber 2061 communicates with the reaction chamber 201 via the inlet microfluidic channel 301. Apply an external force to push the reaction chamber piston 7 upward, and the PCR reaction solution enters the reaction chamber 201, to mix the nucleic acid dissolved in the eluent with a PCR reaction reagent;

Step 12: Apply an external force to push the reaction chamber piston 7 downward, so that the mixed solution in the reaction chamber 201 enters the primary PCR reaction solution chamber 2061 via the inlet microfluidic channel 301. When the liquid level of the mixed solution in the primary PCR reaction solution chamber 2061 is higher than the input port 208 of the primary PCR reaction solution chamber 2061, the mixed solution enters the PCR reaction tube 5 via the input port 208 until the mixed solution overflows from the discharge port 209 of the secondary PCR reaction solution chamber 2062, to complete the liquid inlet of PCR reaction tube 5;

Step 13: Place the PCR reaction tube 5 in a temperature control device, and carry out nucleic acid fluorescent PCR amplification or fluorescent isothermal amplification according to the established PCR amplification program.

In addition, the embodiments described in the following paragraphs are also a part of the present invention.

1. A nucleic acid extraction apparatus, comprising:
a nucleic acid extraction element, a waste storage chamber, and a reaction chamber, wherein the reaction chamber is selectively in communication with the nucleic acid extraction element and the waste storage chamber, and the apparatus realizes fluid exchange through the pressure between the waste storage chamber and the reaction chamber.

2. The apparatus according to paragraph 1, wherein for the apparatus, fluid enters the waste storage chamber from the reaction chamber by reducing the air pressure of the waste storage chamber.

3. The apparatus according to paragraph 2, the air pressure of the waste storage chamber for the apparatus is reduced by a venting element that is in communication with the waste storage chamber.

4. The apparatus according to paragraph 3, wherein the venting element is a columnar suction column.

5. The apparatus according to paragraph 4, wherein the venting element is a cylindrical suction column.

6. The apparatus according to paragraph 5, wherein a gasket is disposed at the junction of the suction column and the waste liquid storage chamber.

7. The apparatus according to paragraph 1, wherein a solid phase material for nucleic acid extraction is disposed in the reaction chamber.

8. The apparatus according to paragraph 7, wherein the solid phase material for nucleic acid extraction is a magnetic bead.

9. The apparatus according to paragraph 1, wherein the nucleic acid extraction element comprises:
a lysis chamber for adding and storing a mixture of sample and lysate; or,
a wash chamber for adding and storing washing liquid; or,
an eluent chamber for adding and storing eluent;
wherein, one or more of the lysis chamber, the wash chamber or the eluent chamber are in fluidic communication with the reaction chamber, respectively.

10. The apparatus according to paragraph 9, wherein the wash chamber comprises a primary wash chamber, a secondary wash chamber and a tertiary wash chamber, one or more of the primary wash chamber, the secondary wash chamber or the tertiary wash chamber being in fluidic communication with the reaction chamber, respectively.

11. The apparatus according to paragraph 1, wherein the apparatus may further comprise a nucleic acid amplification element, and the nucleic acid amplification element is a PCR reaction solution chamber that is in fluidic communication with the reaction chamber, inside of which is provided with reagents for a PCR reaction.

12. The apparatus according to paragraph 11, wherein the nucleic acid amplification element further comprises a PCR reaction tube that is in fluidic communication with the PCR reaction solution chamber.

13. The apparatus according to paragraph 12, wherein a sidewall of the PCR reaction solution chamber is provided with an input port and a discharge port that are in fluidic communication with the PCR reaction tube.

14. The apparatus according to paragraph 13, wherein the PCR reaction solution chamber comprises a primary PCR reaction solution chamber and a secondary PCR reaction solution chamber, wherein the primary PCR reaction solution chamber is in fluidic communication with the reaction chamber, wherein an input port is disposed at the bottom of the sidewall of the primary PCR reaction solution chamber, and a discharge port disposed at the top of the sidewall of the secondary PCR reaction solution chamber.

15. The apparatus according to any one of paragraphs 1 to 14, wherein the apparatus comprises a microfluidic channel for fluidic communication with a reaction chamber, a waste storage chamber, a nucleic acid extraction element or a nucleic acid amplification element.

16. The apparatus according to paragraph 15, wherein the microfluidic channel is radially extended on a rotary disk, and the reaction chamber, the waste storage chamber, the nucleic acid extraction element or the nucleic acid amplification element are in communication with or not in communication with each other by the rotation of the rotary disk.

17. The apparatus according to paragraph 1, wherein the fluid exchange is achieved by a microfluidic channel.

18. The apparatus according to paragraph 1, wherein the waste storage chamber is not in fluidic communication with the reaction chamber when the reaction chamber is in fluidic communication with the nucleic acid extraction element, and the reaction chamber is not in fluidic communication with the nucleic acid extraction element when the waste storage chamber is in fluidic communication with the reaction chamber.

19. The apparatus according to paragraph 18, wherein the apparatus comprises a piston, the fluid in the nucleic acid extraction element enters the reaction chamber by the movement of the piston.

20. The apparatus according to paragraph 19, wherein the movement of the piston is an upward movement along the reaction chamber.

21. The apparatus according to paragraph 20, wherein the apparatus further comprises a venting element that causes the waste storage chamber to generate a negative pressure, thereby allowing the fluid in the reaction chamber to enter the waste storage chamber.

22. The apparatus according to paragraph 21, wherein the negative pressure drives the piston to move downwardly along the reaction chamber.

23. The apparatus according to paragraph 22, wherein the venting element that causes the waste storage chamber to generate a negative pressure is a suction column connected to the waste storage chamber.

24. A method for extracting a nucleic acid, comprising the following steps :
  (1) providing a nucleic acid extraction apparatus, wherein the apparatus comprising: a nucleic acid extraction element for extraction of nucleic acids; a waste storage chamber for storing waste liquid during the reaction; a reaction chamber, being selectivity in communication with the nucleic acid extraction element and the waste storage chamber;
  (2) allowing the reaction chamber to be in fluidic exchange with the waste storage chamber or the nucleic acid extraction element to achieve extraction of nucleic acids.

25. The method according to paragraph 24, wherein the fluid is exchanged between the reaction chamber, the waste storage chamber, or the nucleic acid extraction element by a pressure change between the waste storage chamber and the reaction chamber.

26. The method according to paragraph 25, wherein the fluid is allowed to enter the waste storage chamber from the reaction chamber by reducing the air pressure in the waste storage chamber.

27. The method according to paragraph 26, wherein the air pressure of the waste storage chamber is reduced by a venting element that is in communication with the waste storage chamber.

28. The method according to paragraph 27, wherein the venting element is a cylindrical suction column.

29. The method according to paragraph 24, wherein a solid phase material for nucleic acid extraction is provided in the reaction chamber to bind the nucleic acid in the sample to the solid phase material for nucleic acid extraction.

30. The method according to paragraph 29, wherein the solid phase material for nucleic acid extraction is a magnetic bead.

31. The method according to paragraph 24, wherein the nucleic acid extraction element comprises:
  a lysis chamber for adding and storing a mixture of sample and lysate; or,
  a wash chamber for adding and storing washing liquid; or,
  an eluent chamber for adding and storing eluent;
  wherein, one or more of the lysis chamber, the wash chamber or the eluent chamber are in fluidic communication with the reaction chamber, respectively.

32. The method according to paragraph 31, wherein the wash chamber comprises a primary wash chamber, a secondary wash chamber and a tertiary wash chamber, one or more of the primary wash chamber, the secondary wash chamber or the tertiary wash chamber being in fluidic communication with the reaction chamber, respectively.

33. The method according to paragraph 24, wherein the method further comprises a step of nucleic acid amplification, and the reaction chamber is in fluidic communication with the nucleic acid amplification element to achieve nucleic acid amplification, wherein, the nucleic acid amplification element is a PCR reaction solution chamber that is in fluidic communication with the reaction chamber, inside of which is provided with reagents for a PCR reaction.

34. The method according to paragraph 33, wherein the nucleic acid amplification element further comprises a PCR reaction tube that is in fluidic communication with the PCR reaction solution chamber, to allow fluid to enter the PCR reaction tube for amplification reaction.

35. The method according to paragraph 34, wherein the PCR reaction tube achieves fluidic communication through an input port and a discharge port disposed on sidewall of the PCR reaction solution chamber.

36. The method according to paragraph 35, wherein the PCR reaction solution chamber comprises a primary PCR reaction solution chamber and a secondary PCR reaction solution chamber, the primary PCR reaction solution chamber is in fluidic communication with the reaction chamber, wherein an input port is disposed at the bottom of the sidewall of the primary PCR reaction solution chamber, and a discharge port disposed at the top of the sidewall of the secondary PCR reaction solution chamber.

37. The method according to any one of paragraphs 24 to 36, wherein fluidic communication or exchange between the reaction chamber, the waste storage chamber, the nucleic acid extraction element or the nucleic acid amplification element is achieved by a microfluidic channel disposed on the nucleic acid extraction apparatus.

38. The method according to paragraph 37, wherein the microfluidic channel is radially extended on a rotary disk, and the reaction chamber, the waste storage chamber, the nucleic acid extraction element or the nucleic acid amplification element are in communication with or not in communication with each other by the rotation of the rotary disk.

39. The method according to paragraph 24, wherein the fluid exchange is achieved by a microfluidic channel.

40. The method according to paragraph 24, wherein the waste storage chamber is not in fluidic communication with the reaction chamber when the reaction chamber is in fluidic communication with the nucleic acid extraction element; and the reaction chamber is not in fluidic communication with the nucleic acid extraction element when the waste storage chamber is in fluidic communication with the reaction chamber.

41. The method according to paragraph 40, wherein the fluid in the nucleic acid extraction element enters the reaction chamber by the movement of a piston disposed on the reaction chamber.

42. The method according to paragraph 41, wherein the movement of the piston is an upward movement along the reaction chamber.

43. The method according to paragraph 42, wherein the fluid in the reaction chamber enters the waste storage chamber by a venting element that causes the waste storage chamber to generate a negative pressure.

44. The method according to paragraph 43, wherein the venting element that causes the waste storage chamber to generate a negative pressure is a suction column connected to the waste storage chamber and the negative pressure drives the piston to move downwardly along the reaction chamber.

The foregoing descriptions are merely the preferred embodiments of the present invention, and are not intended to limit the present invention. Any modifications, equivalents, improvements, etc. made without departing from the spirit and scope of the present invention shall fall into the scope of protection of the present invention.

The invention claimed is:
1. A nucleic acid extraction apparatus, comprising:
  a shell which has a plurality of nucleic acid extraction chambers, comprising:

a lysis chamber with lysate reagent for receiving a sample;

a wash chamber for adding and storing a washing liquid;

an eluent chamber for adding and storing an eluent reagent;

a reaction chamber selectively in communication with one or more of the lysis chamber, the wash chamber or the eluent chamber of the plurality of nucleic acid extraction chambers for receiving the sample, the washing liquid, and the eluent reagent subsequently;

a waste storage chamber for receiving a liquid from the reaction chamber;

wherein the nucleic acid extraction apparatus realizes fluid exchange through a pressure difference between the waste storage chamber and the reaction chamber;

a hollow piston disposed in the reaction chamber and configured to move between a first position and a second position in the reaction chamber to change a pressure in the reaction chamber;

a magnetic bead disposed in the reaction chamber for binding a nucleic acid;

a receiving chamber for accommodating a permanent magnet as to fix the magnetic bead on an outer side wall of the receiving chamber;

wherein the receiving chamber is disposed in the hollow piston, and the hollow piston is movable relative to the receiving chamber; and wherein a recess is provided on a sidewall at a bottom of the hollow piston, and when the hollow piston is at the second position, the recess and the outer side wall of the receiving chamber form a space for accommodating the magnetic bead therein;

a columnar suction column having a first end in fluid communication with the waste storage chamber and a second end connected to an air pumping device, wherein when the columnar suction column is used to reduce a pressure in the waste storage chamber, to move the liquid from the reaction chamber to the waste storage chamber, and at the same time to force the piston to move from the first position to the second position; and a first PCR reaction solution chamber and a second PCR reaction solution chamber both in fluidic communication with the reaction chamber, wherein the first PCR reaction solution chamber and the second PCR reaction solution chamber are independent of each other;

a rotary disk disposed at the bottom of the shell, wherein the rotary disk includes a microfluidic channel for fluidic communication with the reaction chamber, the waste storage chamber, the nucleic acid extraction chamber or a PCR reaction solution chamber of the first and second PCR reaction solution chambers;

a PCR reaction tube for completing a PCR reaction, wherein the PCR reaction tube includes a first port and a second port;

wherein an input port is provided at a sidewall of the first PCR reaction solution chamber; a discharge port is provided at a sidewall of the second PCR reaction solution chamber, the input port is in fluid communication with the first port of the PCR reaction tube, the discharge port is in fluid communication with the second port of PCR reaction tube; and wherein a height of the discharge port from a bottom of the second PCR reaction solution chamber is higher than a height of the input port from a bottom of the first PCR reaction solution chamber.

2. The apparatus according to claim 1, wherein a gasket is disposed at a junction of the columnar suction column and the waste storage chamber.

3. The apparatus according to claim 1, wherein a solid phase material for nucleic acid extraction is disposed in the reaction chamber.

4. The apparatus according to claim 1, wherein the wash chamber comprises a primary wash chamber, a secondary wash chamber and a tertiary wash chamber, one or more of the primary wash chamber, the secondary wash chamber or the tertiary wash chamber being in fluidic communication with the reaction chamber.

5. The apparatus according to claim 1, wherein the lysis chamber, the wash chamber, the eluent chamber, the reaction chamber, the waste storage chamber, the first PCR reaction solution chamber, or the second PCR reaction solution chamber are in communication with or not in communication with each other by a rotation of the rotary disk.

6. The apparatus according to claim 1, wherein the waste storage chamber is not in fluidic communication with the reaction chamber when the reaction chamber is in fluidic communication with the lysis chamber, and the reaction chamber is not in fluidic communication with the lysis chamber when the waste storage chamber is in fluidic communication with the reaction chamber.

7. The apparatus according to claim 6, wherein a fluid in the lysis chamber enters the reaction chamber by a movement of the piston.

8. The apparatus according to claim 7, wherein the movement of the piston is an upward movement along the reaction chamber.

* * * * *